(12) United States Patent
Lu

(10) Patent No.: US 7,144,377 B2
(45) Date of Patent: Dec. 5, 2006

(54) PERSONAL CERVICAL CELL COLLECTOR

(76) Inventor: Li-Cheng Lu, 4F., No.2. Lane 847, Jhongshan Rd., Taoyuan City, Taoyuan County (TW)

( * ) Notice: Subject to any disclaimer, the term of this patent is extended or adjusted under 35 U.S.C. 154(b) by 205 days.

(21) Appl. No.: 11/022,695

(22) Filed: Dec. 28, 2004

(65) Prior Publication Data
US 2006/0030786 A1    Feb. 9, 2006

(30) Foreign Application Priority Data
Aug. 6, 2004    (TW) ............................... 93123718 A

(51) Int. Cl.
*A61B 10/00* (2006.01)
(52) U.S. Cl. ................... 600/572; 600/562; 600/563; 600/569; 600/570; 600/571
(58) Field of Classification Search ............... None
See application file for complete search history.

(56) References Cited
U.S. PATENT DOCUMENTS
4,023,559 A * 5/1977 Gaskell ...................... 600/572
5,129,402 A * 7/1992 Koll et al. .................. 600/572
5,535,756 A * 7/1996 Parasher .................... 600/569
2005/0288606 A1 * 12/2005 Alter ......................... 600/572

* cited by examiner

Primary Examiner—Max F. Hindenburg
Assistant Examiner—Anuradha Roy

(57) ABSTRACT

A personal cervical cell collector that will allow a female patient to collect cervical cells in the privacy of her home, having a proximal end and a distal end that has a position unit formed therein, a guide assembly having a head formed in a front end thereof and exposing from the outer shell and a sampling assembly having a sampling unit. The guide assembly mounted in the outer shell is guiding the personal cervical cell collector to insert into the vagina guided by the head, and the head touches the woman's cervix and the position unit locks with a peripheral of the cervix for achieving position effect. Continuously, the guide assembly is taken out and the sampling assembly is mounted and then the sampling unit is adjusted to a direction corresponding to the cervix so that collecting is proceeding.

18 Claims, 9 Drawing Sheets

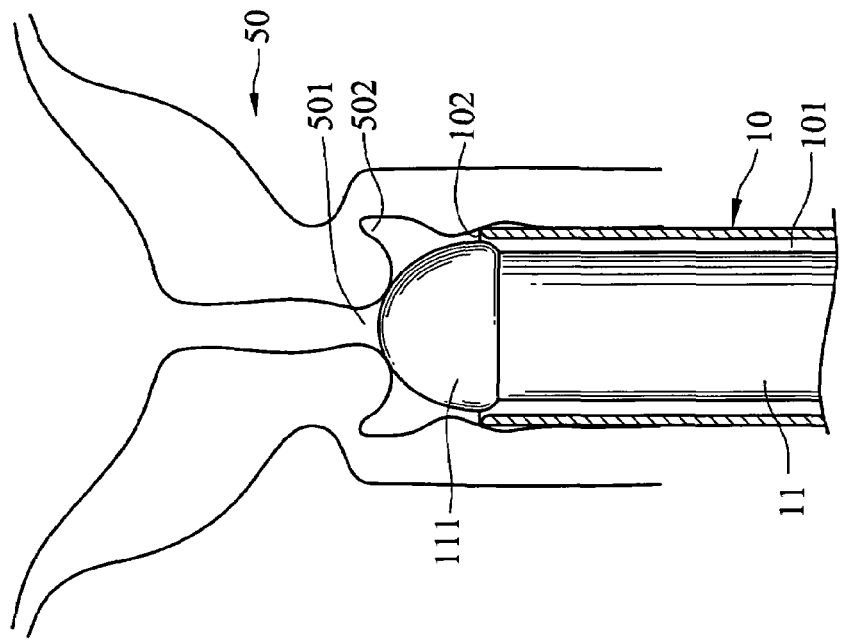
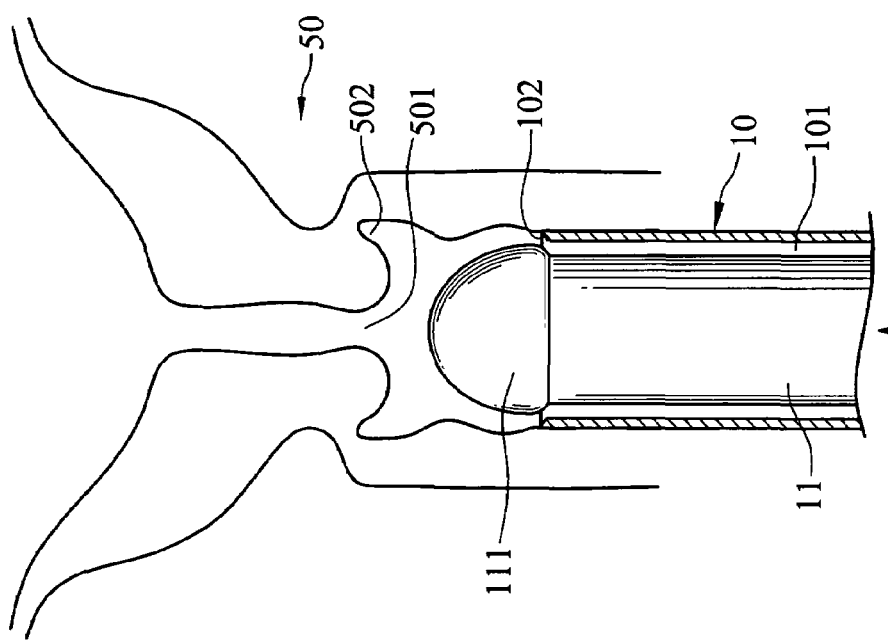
FIG. 2A
FIG. 2B

PERSONAL CERVICAL CELL COLLECTOR

BACKGROUND OF THE INVENTION

The present invention relates in general to a personal cervical cell collector, and more particularly, to a personal cervical cell collector that will allow a female person to collect cervical cells in the privacy of her home.

During the 1940's, Dr. George Papanicolaou developed a screening test which bears his name and which has become the most widely used screening technique for detecting abnormal cervical cells. Today, this test is known more commonly as the PAP test or the PAP smear test. Typically, the PAP smear test is performed in the physician's office as part of a woman's routine gynecological examination. If identified early and treated, deaths of cervical cancer are completely unnecessary because up to 100% of the most common types of cervical cancer may be prevented. Compared with invasive cervical cancer which has a cure rate of 50% to 60% in average, the PAP smear test for screening cervical cancer is of great worth. In cytology, normal cervical cells are columnar cells, have medium-sized nuclear, no hyperchromatic nuclei and no mitotic figures. On the side, if cells have no clear cell border, larger and darker nuclei, increased nuclear/cytoplasmic area ratio, increased mitotic figures and a disorderly arrangement, the cells are abnormal. The clinical classification of the abnormal cells has five degrees as follows. The defined class I is normal, class II is inflammation or atrophy (like a menopause variation), class III is cervical dysplasia (between normal cells and cancer cells), class IV is pre-cancer cell (carcinoma in situ), and class V is malignancy.

Typically, the PAP test is performed by inserting a speculum into the patient's vagina to expose the cervix. The surface of the cervix is then scraped by a brush, stick or swab and the exfoliated cells thereby collected are smeared upon a microscope slide for cytological examination.

However, the conventional smear test needs to collect cervical cells firstly and that process needs to insert a collector like stick or swab into the patient's vagina and then reach to the cervix. If the collector is not inserting enough to reach to the cervix, the exfoliated cells collected have no means because of the collected cells are vagina epidermal cells if the location the collector reached is too shallow and it is easy to cause a erroneous judgment. On the contrary, the collected cells are endometrial cells if the collector is inserting too deep and the uterus also may be injured by the collector.

Furthermore, the PAP smear test is nearly always performed in a physician's office by a gynecologist or other medical professional who almost is male. Thus, the test is considered by many women to be uncomfortable and embarrassing. Therefore, a personal cervical cell collector that will allow a female patient to collect cervical cells in the privacy of her home is required.

BRIEF SUMMARY OF THE INVENTION

The present invention provides a personal cervical cell collector that has a simple positional function for collecting cervical cells correctly by users themselves such that collecting wrong cells will not happen.

A personal cervical cell collector in accordance with the present, which will allow a female patient to collect cervical cells in the privacy of her home, having a proximal end and a distal end that has a position unit formed therein, a guide assembly having a head formed in a front end thereof and exposing from the outer shell and a sampling assembly having a sampling unit. The guide assembly mounted in the outer shell is used for guiding the personal cervical cell collector to insert into the vagina, and the head touches the woman's cervix and the position unit locks with a peripheral of the cervix for achieving position effect. Continuously, the guide assembly is taken out and the sampling assembly is mounted in and then the sampling unit is adjusted to a direction corresponding to the cervix so that collecting is proceeding.

The objectives of the present invention will become obvious to those of ordinary skill in the art after reading the following detailed description of preferred embodiments.

It is to be understood that both the foregoing general description and the following detailed description are exemplary, and are intended to provide further explanation of the invention as claimed.

BRIEF DESCRIPTION OF THE DRAWINGS

These as well as other features of the present invention will become more apparent upon reference to the drawings therein:

FIG. 2A to 2F are operative views of the first embodiment of the personal cervical cell collector in FIG. 1.

DETAILED DESCRIPTION OF THE INVENTION

Figure 1C:
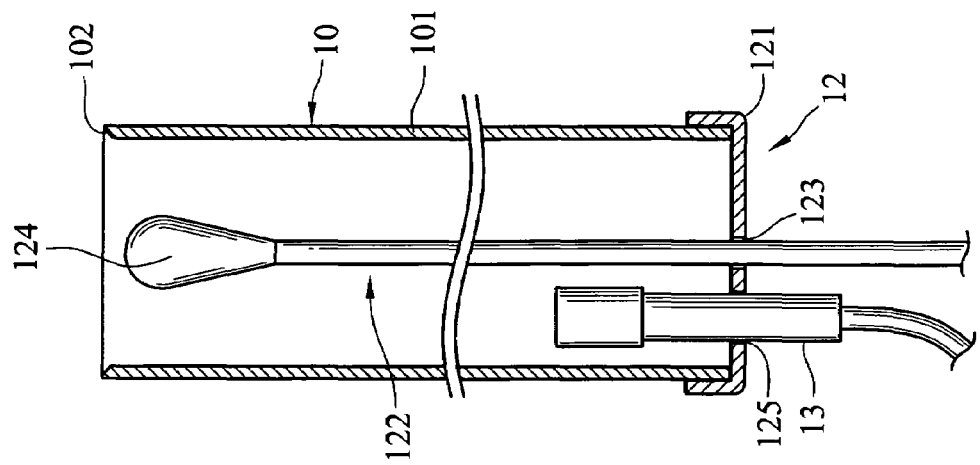
FIG. 1C is a plan view of the first embodiment of the personal cervical cell collector in FIG. 1B connected with a camera.

Reference will now be made in detail to the preferred embodiments of the present invention, examples of which are illustrated in the accompanying drawings. Wherever possible, the same reference numbers are used in the drawings and the description to refer to the same or like parts.

Figure 1B:
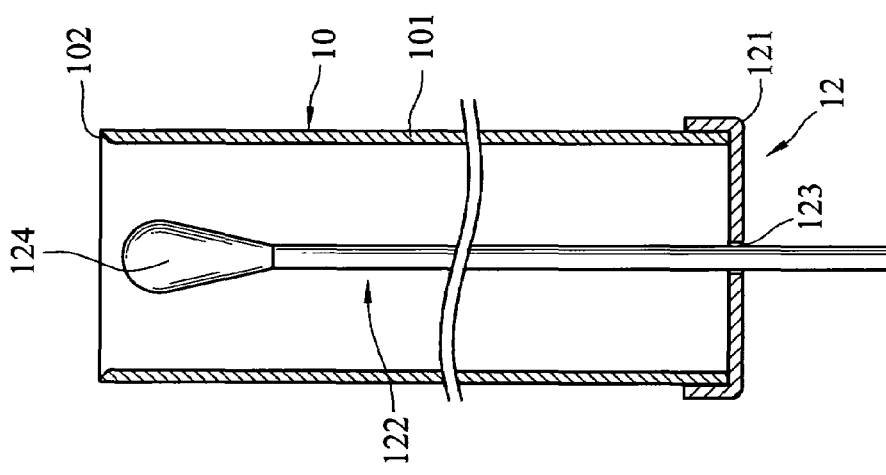
FIG. 1B is a plan view of the outer shell connected with a sampling assembly of the first embodiment of the personal cervical cell collector in FIG. 1A.
Figure 1A:
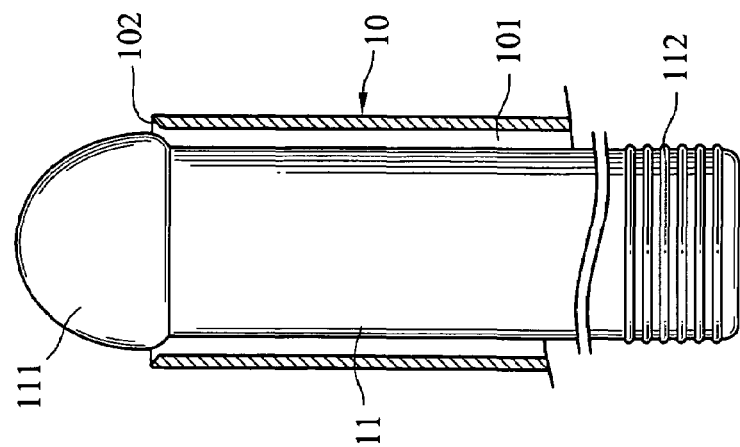
FIG. 1A is a plan view of an outer shell connected with a guide assembly of a first embodiment of a personal cervical cell collector in accordance with the present invention.

Referring to FIGS. 1A and 1B, a personal cervical cell collector in accordance with the present invention, which can be used for collecting cervical cells in the privacy of woman's home by herself to be detected, comprises an outer shell 10, a guide assembly 11 and a sampling assembly 12. The outer shell 10 is tubular and has a capacity 101 therein for selectively assembling with the guide assembly 11 (see FIG. 1A) or the sampling assembly 12 (see FIG. 1B), a proximal end and a distal end. The outer shell 10 has an outer diameter that is almost the same as an inner diameter of woman's vagina and preferably the outer diameter thereof is variety dependent on nature difference and different childbirth experiment from women. The outer shell 10 has a position unit 102 formed in the distal end for positing the outer shell 10 to a correct site, and preferably a wall of the outer shell 10 near the distal end is narrow gradually. More preferably, the wall of the outer shell 10 near the distal end has a bevel design for preventing from injuring vagina.

The guide assembly 11 is selectively mounted in the capacity 101 of the outer shell 10 and has a proximal end, a distal end and a smooth head 111 formed on the proximal end. The head 111 can be hollow or solid cylinder for facilitating users insert the collector into the vagina. Preferably, the head 111 can be similar to man's glans penis or a smooth curve or an arc-shape. A largest diameter of the head 111 is almost the same as an inner diameter of the capacity 101 of the outer shell 10 so that the guide assembly 11 will not depart from the outer shell 10 when the guide assembly 11 mounted in the outer shell 10 and a front part of the head 111 can expose from the outer shell 10 for guiding the collector into the vagina. Furthermore, the guide assembly 11 preferably has a skidproof portion 112 formed on the distal end thereof.

The sampling assembly 12 is selectively mounted in the capacity 101 of the outer shell 10 and has a holder 121 and a sampling unit 122. The holder 121 is a circular cover and has a hole 123 formed in a center thereof. The sampling unit 122 is mounted and rotated through the hole 123 and has a collecting part 124 formed in a front end thereof for collecting cervical cells.

With further reference to FIG. 1C, the personal cervical cell collector in accordance with the present invention further comprises a camera 13 mounted in a connecting hole 125 in the sampling assembly 12 for facilitating users use. Preferably, the connecting hole 125 is formed in the holder 121. Through the camera 13 to show figures, users can be more convenient to collect cervical cells. Of course, the camera 13 can connect with a lighting unit or a colposcopy for helping collecting.

Figure 2C:
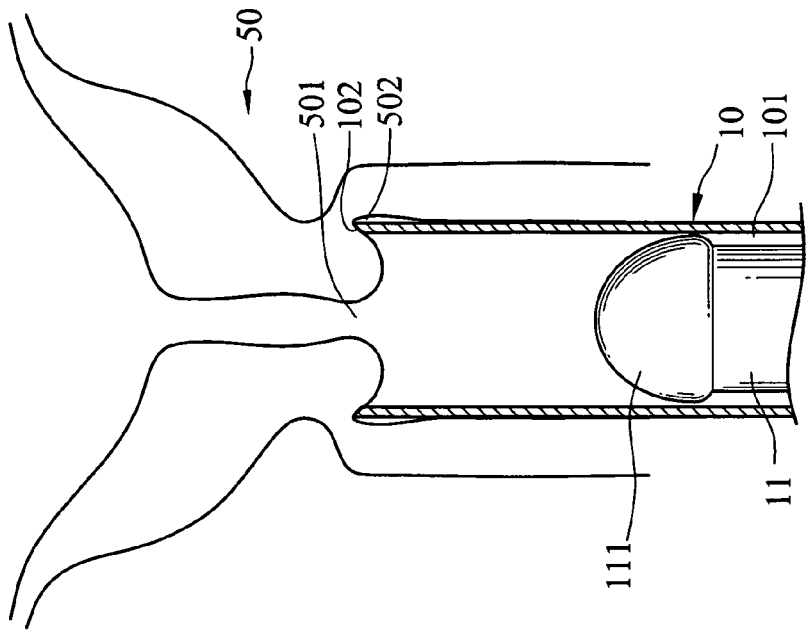

When using, the guide assembly 11 mounted in the outer shell 10 and the head 111 exposing from the distal end of the outer shell 10. The user can easily put the guide assembly 11 with the outer shell 10 into the vagina guiding by the smooth head 111 (see FIG. 2A) until the head 111 arriving and touching to the cervix 501 (see FIG. 2B). Because of the smooth design of the head 111, the guide assembly 11 not only guides the collector into the vagina but also protect the vagina, uterus 50, cervix 501 from injuring. Then, the outer shell 10 continues to go inside until the position unit 102 on the distal end of outer shell 10 locking with a peripheral 502 of the cervix (see FIG. 2C). That is the point why users can collect cervical cells by themselves and not injury vagina or cervix 501 or collect wrong cells.

Figure 2D:
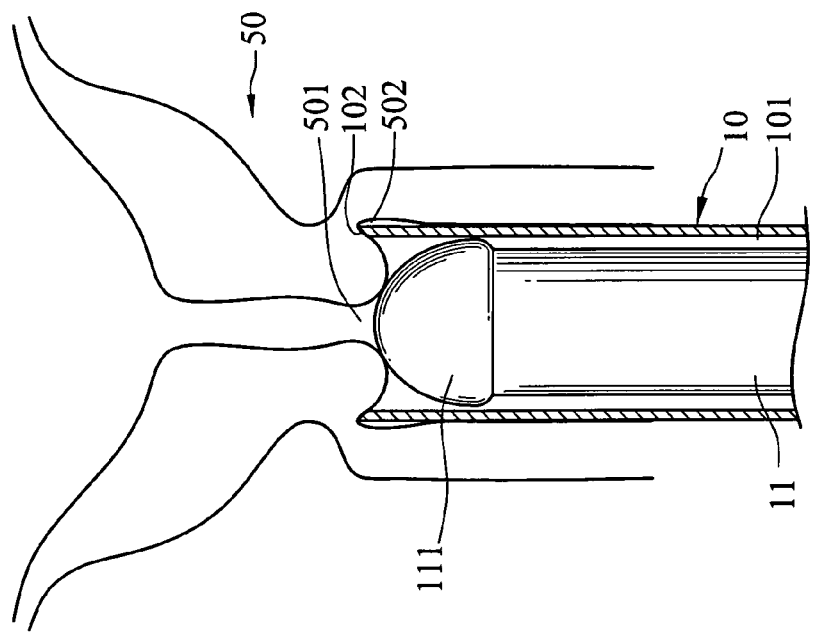
Figure 2E:
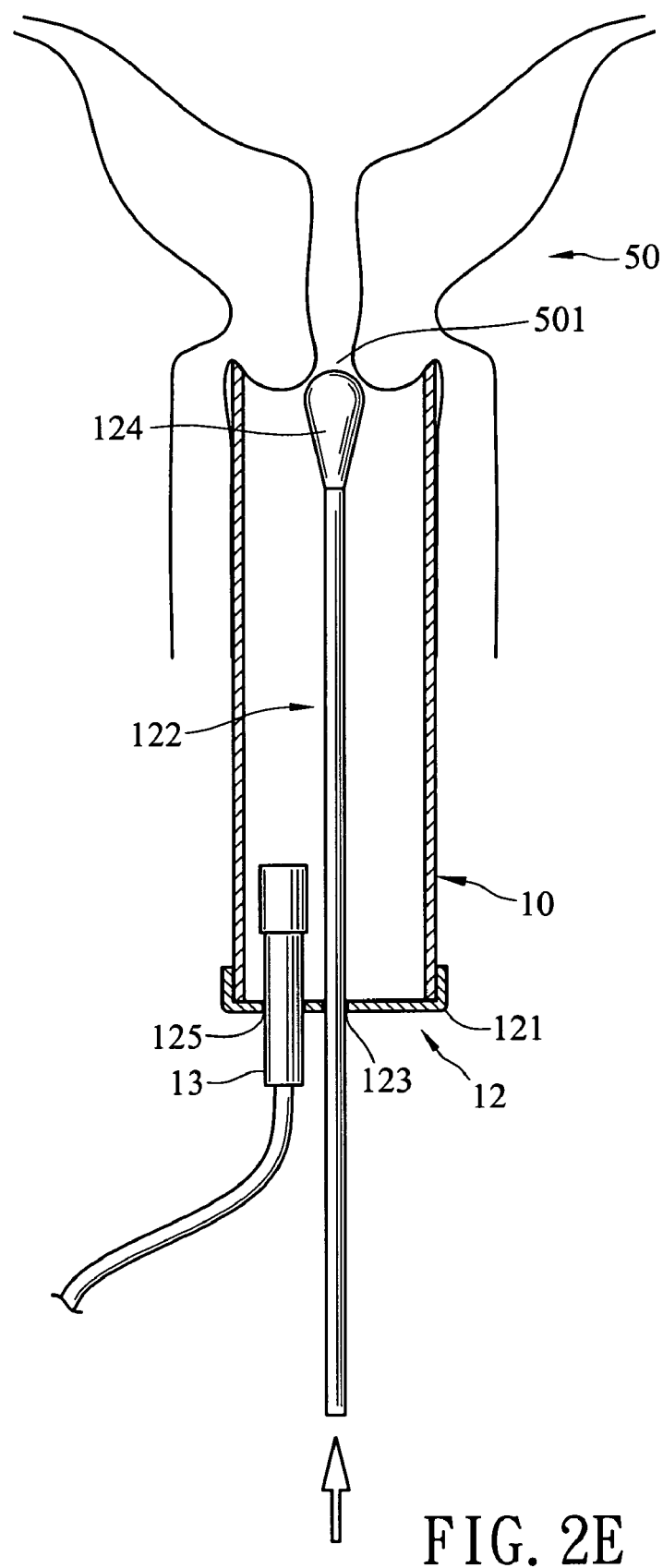
Figure 2F:
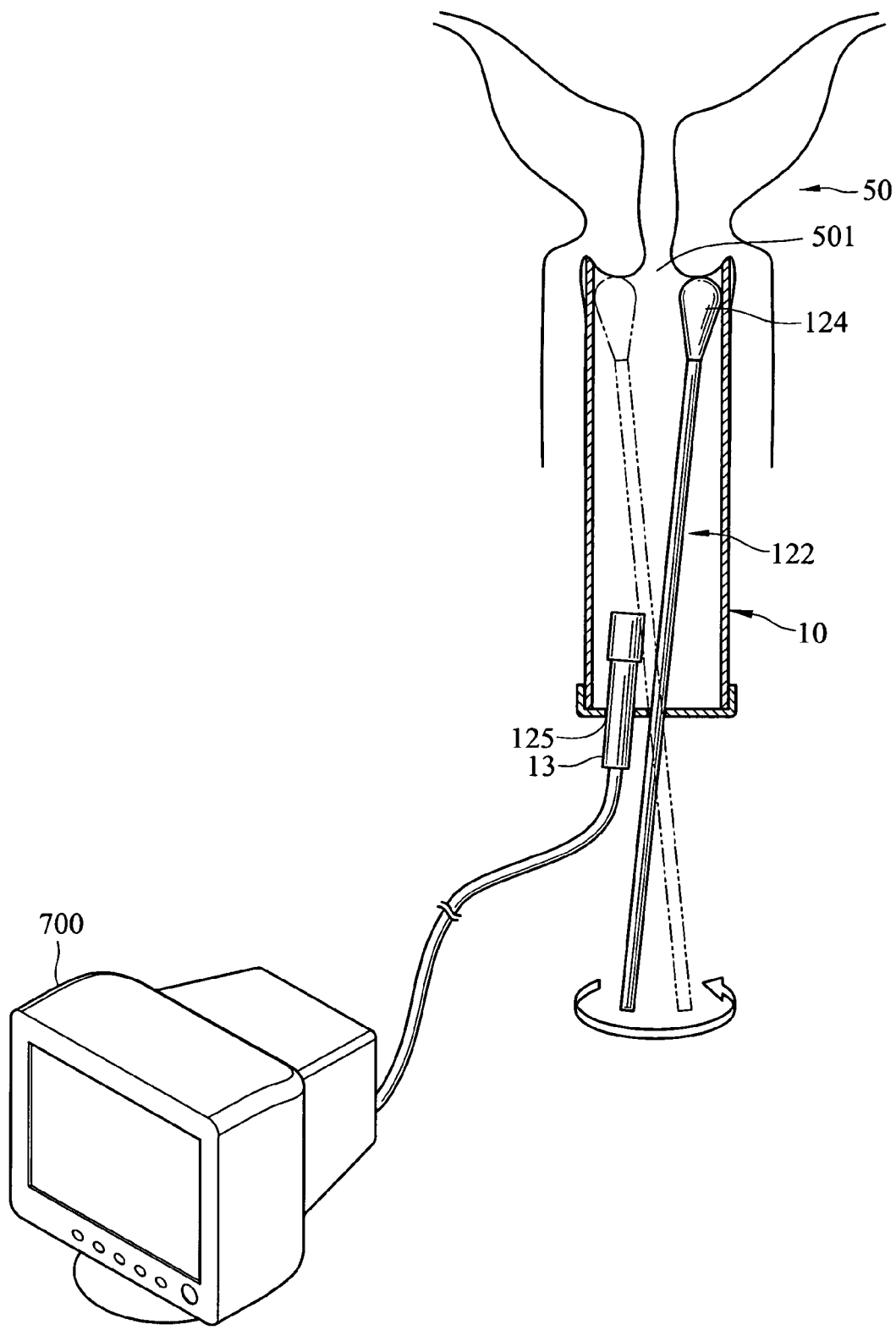

Following, the guide assembly 11 is taken out (see FIG. 2D) and the sampling assembly 12 is mounted (see FIG. 2E). Turning the sampling unit 122 makes the collecting part 124 posit at the cervix 501 and the collecting part 124 is performed to collect cells (see FIG. 2F). During collecting, the camera 13 can connect to a display unit 700 for observing status of collection and users can adjust collection direction of the sampling unit 122 at the same time such that an objective of indeed collecting is achieved. The collected cells can be detected by using variety marketed test or by doctors in hospital.

Figure 3B:
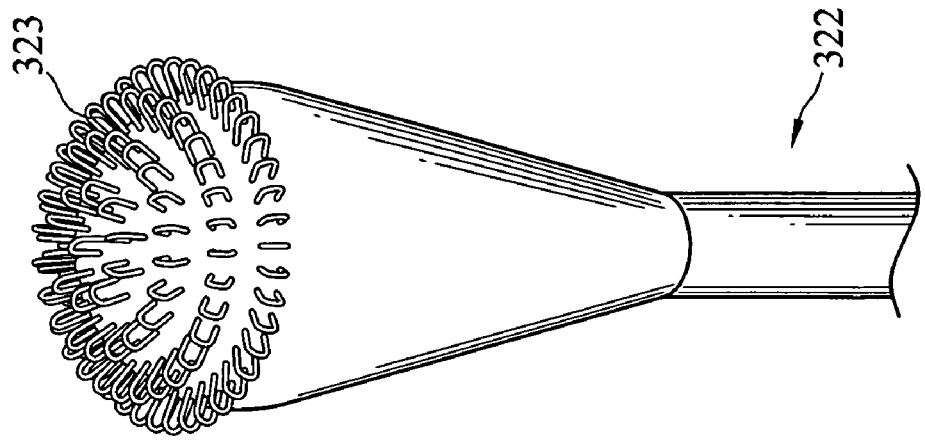
FIG. 3B is a perspective view of a third embodiment of a sampling unit of a personal cervical cell collector in accordance with the present invention.
Figure 3A:
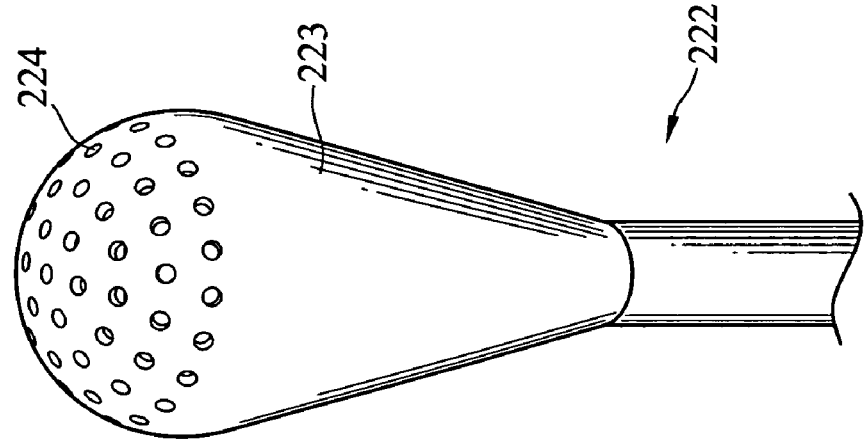
FIG. 3A is a perspective view of a second embodiment of a sampling unit of a personal cervical cell collector in accordance with the present invention.

The sampling unit 122 in accordance with the present invention can be various types. With reference to FIG. 3A, a second embodiment of a sampling unit 222 comprises a watering unit 223 and a plurality of watering holes 224. The watering unit 223 is mounted in the sampling unit 222 and the watering holes 224 are formed in a front end of the sampling unit 222. Water can spurt from the watering holes 224 spurting by the watering unit 223 for rinsing out partial cervical cells. With further reference to FIG. 3B, a third embodiment of a sampling unit 322 comprises a plurality of soft brushes 323 for brushing partial cervical cells directly. Of course, the sampling unit has variable types and not to be limited in these two types.

Figure 4:
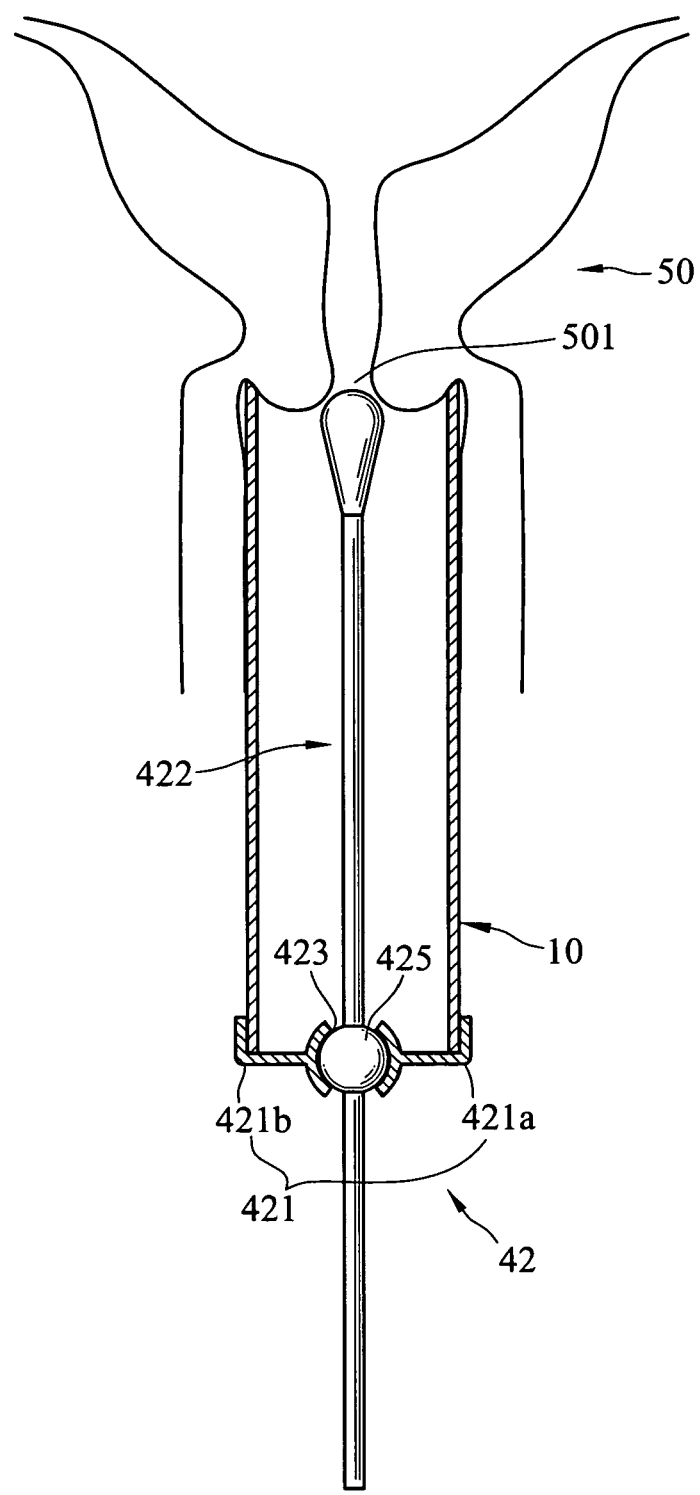
FIG. 4 is a plan view of a fourth embodiment of a sampling assembly of a personal cervical cell collector in accordance with the present invention.

Besides, foregoing embodiments of the sampling unit are still mounted in the hole 123 of the holder 121 but the sampling unit is not to be limited in this type. With reference to FIG. 4, a fourth embodiment of a sampling assembly 42 comprises a sampling unit 422 which clips with a holder 421 of a sampling assembly 42. The holder 421 of the sampling assembly 42 comprises a first clipper 421a and a second clipper 421b. The first clipper 421a and the second clipper 421b form a controlling hole 423 that is a sphere-shape space. The sampling unit 422 comprises a controlling protrusion 425 that has a size a few smaller than the controlling hole 423 and is a sphere-shape. The controlling protrusion 425 is clipped by the first clipper 421a and the second clipper 421b so that the controlling protrusion 425 is controlled in the controlling hole 423 and the sampling unit 422 can rotate as wished.

Figure 5A:
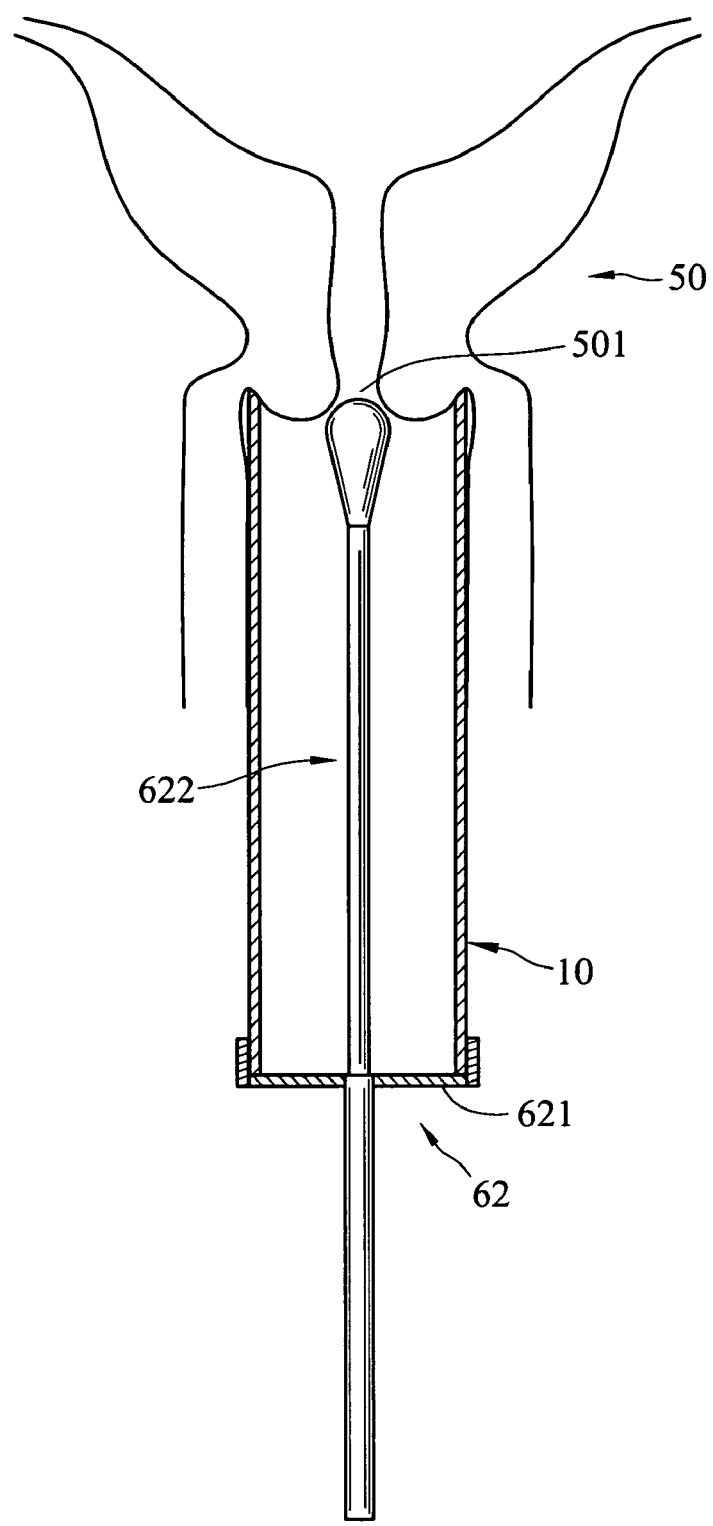
FIG. 5A is a fifth embodiment of a sampling assembly of a personal cervical cell collector in accordance with the present invention.
Figure 5B:
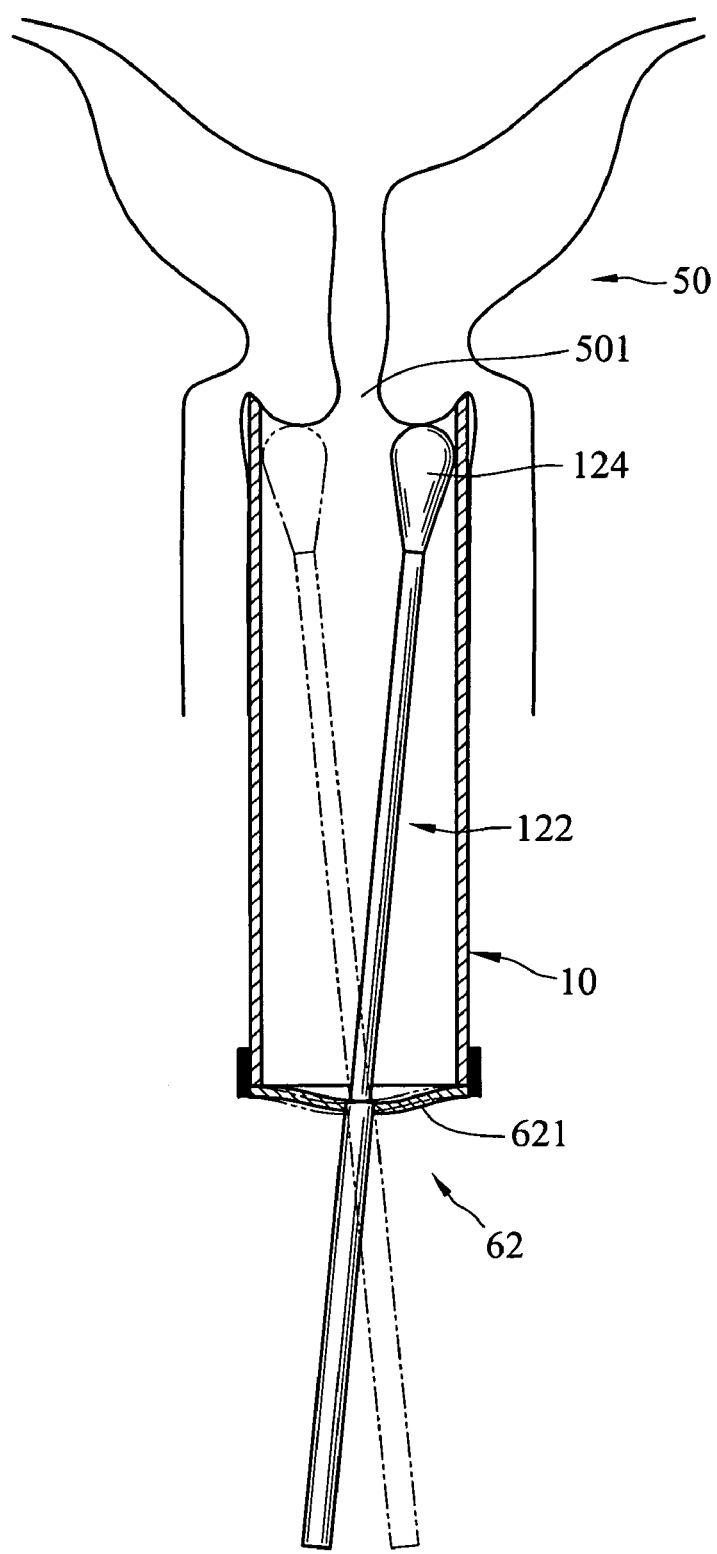
FIG. 5B is an operative view of the fifth embodiment of the sampling assembly in FIG. 5A.

Otherwise, with reference to FIGS. 5A and 5B, a fifth embodiment of a sampling assembly 62 in accordance with the present invention comprises a holder 621 that is a resilient unit and has a wind property so that the holder can turn at any direction and connected with a sampling unit 622. Thereby, the sampling unit 622 is connected with the holder 621 and achieves the same effect of adjusting the sampling unit 622 to posit exactly corresponding to the cervix 501 as the foregoing embodiments done.

While an illustrative and presently preferred embodiment of the invention has been described in detail herein, it is to be understood that the inventive concepts may be otherwise variously embodied and employed and that the appended claims are intended to be construed to include such variations except insofar as limited by the prior art.

What is claimed is:

1. A personal cervical cell collector, comprising:
   a tubular outer shell comprising an outer diameter almost the same as woman's vagina, a proximal end and a distal end that has a circular position unit formed therein;
   a guide assembly selectively mounted in the outer shell and comprising a smooth head formed in a proximal end thereof and exposing from the outer shell; and
   a sampling assembly selectively mounted in the outer shell and comprising a hanging sampling unit which comprises a collecting part formed in a front end thereof;
   whereby, the guide assembly mounted in the outer shell guides the personal cervical cell collector to insert into the vagina guided by the head, and the head touches the woman's cervix and the position unit locks with a peripheral of the cervix for achieving position effect, continuously, the guide assembly is taken out and the sampling assembly is mounted and then the sampling unit is adjusted to a direction corresponding to the cervix so that collecting is proceeding.

2. The personal cervical cell collector of claim 1, wherein the head of the guide assembly has an outer diameter almost the same as an inner diameter of the outer shell.

3. The personal cervical cell collector of claim 2, wherein the head is a man's glans penis shape.

4. The personal cervical cell collector of claim 1, wherein the guide assembly is tubular or solid cylinder.

5. The personal cervical cell collector of claim 1, wherein a wall near the distal end of the outer shell is narrow gradually to form the position unit.

6. The personal cervical cell collector of claim 5, wherein a front end of the position unit has a bevel design for protecting the cervix from injuring.

7. The personal cervical cell collector of claim 1, wherein a front end of the collecting part of the sampling unit comprises a plurality of soft brushes.

8. The personal cervical cell collector of claim 1, wherein the sampling unit further comprises a watering unit mounted in the sampling unit and a plurality of watering holes formed in the front end of the sampling unit and thereby water spurt from the watering hole spurting by the watering unit for rinsing out partial cervical cells.

9. The personal cervical cell collector of claim 1, wherein the sampling assembly further comprises a holder for holding the sampling unit.

10. The personal cervical cell collector of claim 9, wherein the holder comprise a hole for mounting the sampling unit.

11. The personal cervical cell collector of claim 9, wherein the holder is a resilient unit connected with the sampling unit and thereby controlling the holder will adjust the action of the sampling unit.

12. The personal cervical cell collector of claim 9, wherein the holder comprises a first clipper and a second clipper and thereby the sampling unit holds between the first clipper and the second clipper.

13. The personal cervical cell collector of claim 12, wherein the sampling unit further comprises a controlling protrusion clipped between the first clipper and the second clipper and thereby the sampling unit is connected with the holder.

14. The personal cervical cell collector of claim 1, further comprising a camera for observing a status of collection.

15. The personal cervical cell collector of claim 14, wherein the sampling assembly further comprises a connecting hole for mounting the camera.

16. The personal cervical cell collector of claim 15, wherein the connecting hole is formed in the holder of the sampling assembly.

17. The personal cervical cell collector of claim 16, wherein the camera further connects with a lighting unit, a colposcopy or a display unit.

18. The personal cervical cell collector of claim 1, wherein the guide assembly further comprises a skidproof portion formed on the distal end thereof.

* * * * *